(12) United States Patent
Yamada et al.

(10) Patent No.: US 7,942,834 B2
(45) Date of Patent: May 17, 2011

(54) ENDOSCOPE WITH ULTRASONIC VIBRATION ISOLATING PROTRUSIONS

(75) Inventors: Norihiro Yamada, Tokyo (JP); Hironobu Ichimura, Tokyo (JP)

(73) Assignee: Olympus Corporation (JP)

( * ) Notice: Subject to any disclaimer, the term of this patent is extended or adjusted under 35 U.S.C. 154(b) by 930 days.

(21) Appl. No.: 10/987,700

(22) Filed: Nov. 12, 2004

(65) Prior Publication Data

US 2005/0203418 A1    Sep. 15, 2005

(30) Foreign Application Priority Data

Mar. 10, 2004   (JP) ................. 2004-067943

(51) Int. Cl.
*A61B 8/00* (2006.01)
(52) U.S. Cl. ..................... 601/2; 600/104; 600/462
(58) Field of Classification Search .......... 600/121, 600/439, 104; 601/2, 3; 604/22; 606/128
See application file for complete search history.

(56) References Cited

U.S. PATENT DOCUMENTS

| | | | | |
|---|---|---|---|---|
| 4,750,902 A | * | 6/1988 | Wuchinich et al. | 604/22 |
| 5,322,055 A | * | 6/1994 | Davison et al. | 601/2 |
| 5,449,370 A | * | 9/1995 | Vaitekunas | 606/169 |
| 5,935,144 A | * | 8/1999 | Estabrook | 606/169 |
| 5,944,737 A | * | 8/1999 | Tsonton et al. | 606/205 |
| 5,957,943 A | * | 9/1999 | Vaitekunas | 606/169 |
| 5,968,060 A | * | 10/1999 | Kellogg | 606/169 |
| 6,056,735 A | * | 5/2000 | Okada et al. | 606/1 |
| 6,117,152 A | * | 9/2000 | Huitema | 606/169 |
| 6,206,844 B1 | * | 3/2001 | Reichel et al. | 601/2 |
| 6,458,142 B1 | * | 10/2002 | Faller et al. | 606/169 |
| 6,544,278 B1 | * | 4/2003 | Vrba et al. | 606/198 |
| 6,773,444 B2 | * | 8/2004 | Messerly | 606/169 |
| 2004/0230111 A1 | * | 11/2004 | Smith et al. | 600/407 |

FOREIGN PATENT DOCUMENTS

| | | |
|---|---|---|
| JP | 62-299251 | 12/1987 |
| JP | 63-73948 | 4/1988 |
| JP | 02-139615 | 5/1990 |
| JP | 04-364835 | 12/1992 |
| JP | 2000-316870 | 11/2000 |
| JP | 2001-037768 | 2/2001 |
| JP | 2001-128988 | 5/2001 |
| JP | 2001-346806 | 12/2001 |
| JP | 2003-010201 | 1/2003 |
| JP | 2004-000336 | 1/2004 |

OTHER PUBLICATIONS

Japanese Office Action dated Oct. 21, 2008 (with English translation).

* cited by examiner

*Primary Examiner* — Brian Casler
*Assistant Examiner* — Jonathan G Cwern
(74) *Attorney, Agent, or Firm* — Ostrolenk Faber LLP (57) ABSTRACT

An endoscope includes an inserted unit for being inserted into a celomic cavity of a body and having therein at least one channel, and an ultrasonic treatment apparatus including a transmitting member that transmits an ultrasonic wave produced by an ultrasonic vibrator, and a treatment unit provided on a distal end of the transmitting member and for being inserted, together with the transmitting member, into the channel. The ultrasonic treatment apparatus is arranged within the channel by positioning a distal end of the treatment unit within a field of vision of the endoscope.

2 Claims, 13 Drawing Sheets

ENDOSCOPE WITH ULTRASONIC VIBRATION ISOLATING PROTRUSIONS

CROSS-REFERENCE TO RELATED APPLICATIONS

This application is based upon and claims the benefit of priority from the prior Japanese Patent Application No. 2004-067943 filed on Mar. 10, 2004; the entire contents of which are incorporated herein by reference.

BACKGROUND OF THE INVENTION

1) Field of the Invention

The present invention relates to an endoscope including a channel for inserting an ultrasonic treatment apparatus into a celomic cavity of a body.

2) Description of the Related Art

There is conventionally employed an endoscope that observes a celomic cavity of a body by inserting the endoscope thereinto, and that performs various treatments and procedures on an affected part (see, for example, Japanese Patent Application Laid-Open No. S62-299251). According to the endoscope disclosed in the application No. S62-299251, a forceps port of the endoscope is inserted into a celomic cavity of a body, and an ultrasonic transmitting member of the ultrasonic treatment apparatus is further inserted into the celomic cavity through the inserted forceps port. Then a distal end of the endoscope is operated to be bent while protruding a distal end of the ultrasonic transmitting member from the distal end of the endoscope. The distal end of the ultrasonic transmitting member is thereby brought into contact with a calculus in the body. By actuating an ultrasonic vibrator of the ultrasonic treatment apparatus in this state, the calculus is broken into pieces.

Generally, the ultrasonic transmitting member utilizes a highest-amplitude part of the ultrasonic vibration. Due to this, according to the conventional endoscope, the ultrasonic transmitting member needs to be set to have a predetermined length so that the distal end thereof is located at the highest-amplitude part of the transmitted ultrasonic vibration. In addition, a treatment unit provided on the distal end needs to be positioned within a field of vision of the endoscope. However, the ultrasonic transmitting member of the conventional endoscope includes no unit that positions the treatment unit on the distal end within the field of vision of the endoscope. It may be, therefore, disadvantageously difficult to position the treatment unit of the ultrasonic transmitting member at an appropriate position when the endoscope is used. Therefore, the conventional endoscope may not be user friendly, and it may be disadvantageously difficult to utilize the ultrasonic transmitting member so that it constantly and stably perform its function as designed.

According to the conventional ultrasonic treatment apparatus, the ultrasonic transmitting member is long and the ultrasonic vibration is transmitted by this ultrasonic transmitting member. As the result, a noise vibration resulting from the ultrasonic vibration thus transmitted and different from the ultrasonic vibration may occur to the ultrasonic transmitting member of the ultrasonic treatment apparatus. If such noise vibration occurs, the ultrasonic transmitting member may interfere with a channel in the endoscope, an unpleasant sound called "chatter" is produced, and stable transmission of the ultrasonic vibration may be hampered.

SUMMARY OF THE INVENTION

It is an object of the present invention to solve at least the problems in the conventional technology.

The endoscope according to one aspect of the present invention includes an inserted unit for being inserted into a celomic cavity of a body and having therein at least one channel; and an ultrasonic treatment apparatus including a transmitting member that transmits an ultrasonic wave produced by an ultrasonic vibrator, and a treatment unit provided on a distal end of the transmitting member and for being inserted, together with the transmitting member, into the channel, wherein the ultrasonic treatment apparatus is arranged within the channel by positioning a distal end of the treatment unit within a field of vision of the endoscope.

The endoscope according to one aspect of the present invention is a medical endoscope, which may be either a so-called rigid endoscope having a metallic sheath provided on an inserted unit inserted into the celomic cavity of the body (see, for example, Japanese Patent Application Laid-Open No. 2000-237118) or a so-called soft endoscope constituted so that an inserted unit inserted into the celomic cavity of the body is formed to be bendable (see, for example, Japanese Patent Application Laid-Open No. H7-325257).

DETAILED DESCRIPTIONS

Exemplary embodiments of an endoscope relating to the present invention will be explained in detail below with reference to the accompanying drawings. However, it should be noted that the present invention is not limited by these embodiments.

Figure 1:
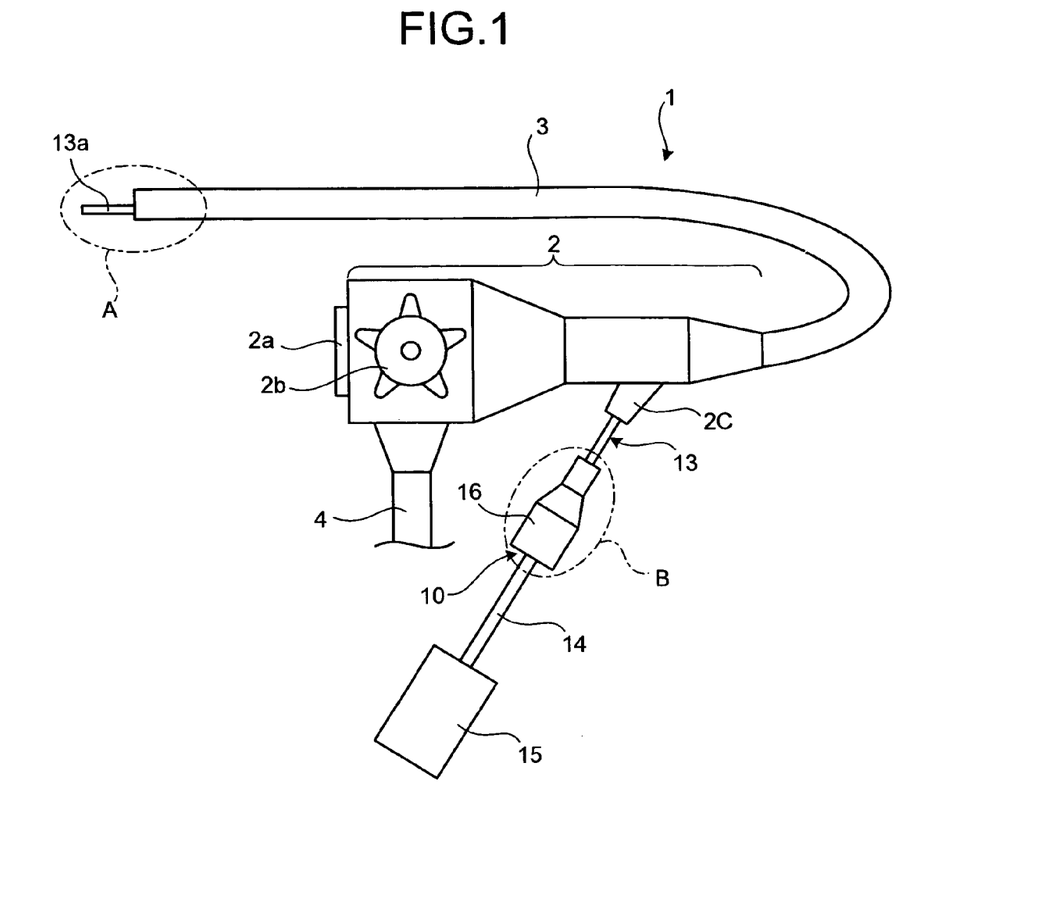
FIG. 1 is a schematic block diagram of an endoscope according to a first embodiment of the present invention.
Figure 2:
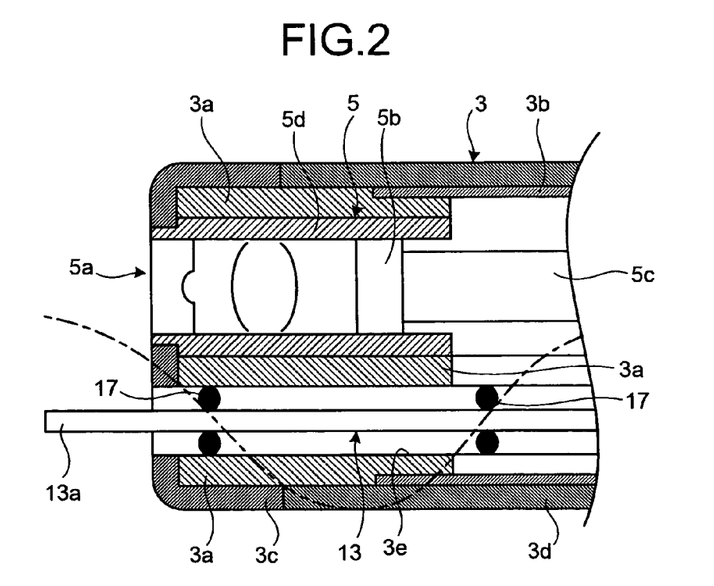
FIG. 2 is an enlarged cross-sectional view of a part A of the endoscope shown in FIG. 1.
Figure 3:
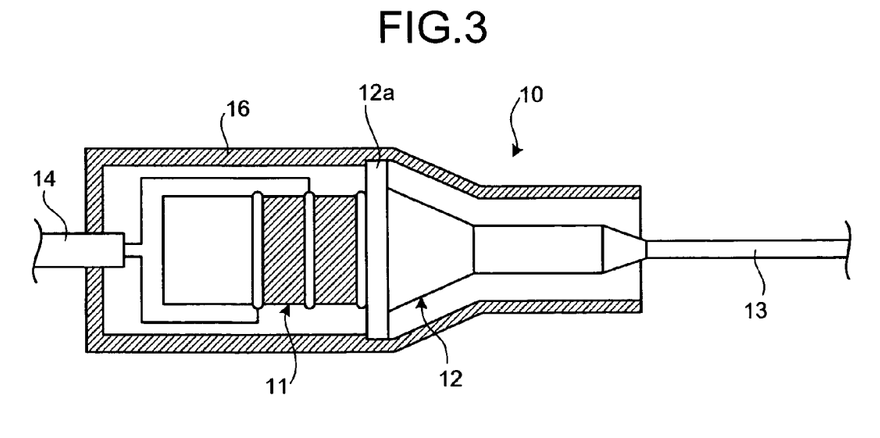
FIG. 3 is an enlarged cross-sectional view of a part B of the endoscope shown in FIG. 1.

FIG. 1 is a schematic block diagram of an endoscope according to the first embodiment. FIG. 2 is an enlarged cross-sectional view of a part A of the endoscope shown in FIG. 1. FIG. 3 is an enlarged cross-sectional view which depicts a part B of the endoscope shown in FIG. 1.

As shown in FIG. 1, an endoscope 1 is a soft endoscope which includes an operating unit 2, an inserted unit 3 connected to the operating unit 2, and an ultrasonic treatment apparatus 10. The inserted unit 3 inserted into a celomic cavity of a body is bendable.

The operating unit 2 is gripped by a user to operate the endoscope 1, and has an eyepiece 2a provided on one end and an operation dial 2b provided on one side surface. The operation dial 2b is connected to a curved bridge 3b, to be explained later, of the inserted unit 3 by an angle wire (not shown). By rotating the operation dial 2b, the inserted unit 3 is bent in a desired direction. In addition, a light guide cable 4 which introduces a light used to observe an interior of the celomic cavity from a light source (not shown) is connected to the operating unit 2. The operating unit 2 also includes a mouthpiece 2c for inserting the ultrasonic treatment apparatus 10 into a channel 3e formed in the inserted unit 3.

As shown in FIG. 2, the inserted unit 3 includes distal end hardware 3a and the curved bridge 3b connected to a rear portion of the distal end hardware 3a. By connecting a plurality of bent bridges 3b, the inserted unit 3 is assembled into a bendable unit. An outer periphery of a front end of the inserted unit 3 is covered with an insulating cover 3c, and a rear portion of the insulating cover 3c is further covered with a rubber tube 3d. The channel 3e for inserting a flexible probe 13 of the ultrasonic treatment apparatus 10 is formed within the inserted unit 3, and an imaging device 5 formed integrally with the distal end hardware 3a is contained within the inserted unit 3. A light guide (not shown) which transmits an observation illuminating light introduced from the light guide cable 4 to a distal end of the inserted unit 3 is contained and arranged within the inserted unit 3.

The imaging device 5 includes an objective lens system 5a, a charge coupled device (CCD) 5b, and an electric cable 5c which extends through a circuit board. The imaging device 5 is formed integrally with the distal end hardware 3a through an attachment frame 5d.

As shown in FIGS. 1 and 3, the ultrasonic treatment apparatus 10 includes an ultrasonic vibrator 11 and a flexible probe 13 which is long. The ultrasonic vibrator 11 is a Langevin-type vibrator including a horn 12 and is fastened by a bolt, and connected to a power supply 15 by a power cable 14. In the ultrasonic treatment apparatus 10, by fixing a flange 12a of the horn 12, the ultrasonic vibrator 11 and the horn 12 are contained and fixed into a casing 16. The flexible probe 13 is a flexible transmitting member that transmits an ultrasonic wave produced by the ultrasonic vibrator 11, and is made of metal such as titanium alloy, nickel alloy, stainless steel, or duralumin, a quartz fiber, or the like.

It is assumed herein that the flexible probe 13 is the transmitting member a shape of which is substantially returned to an original shape by elastic deformation when the probe 13 is bent at, for example, 90 degrees or more to exhibit flexibility. A treatment unit 13a provided on a distal end of the flexible probe 13 protrudes from the channel 3e into the celomic cavity of the body by a predetermined length so that it can be used to perform a medical treatment. To this end, a length of the flexible probe 13 is set based on a vibration frequency of the ultrasonic vibrator 11 according to the flange 12a which is a node of the ultrasonic vibration so that the distal end of the treatment unit 13a is located on the highest-amplitude part of the ultrasonic vibration.

At this moment, the distal end of the treatment unit 13a of the flexible probe 13 of the ultrasonic treatment apparatus 10 is positioned within a field of vision of the endoscope 1 and arranged in the channel 3e. Therefore, in the endoscope 1, the mouthpiece 2c and the casing 16 constitute a positioning unit that positions the ultrasonic treatment apparatus 10. Namely, as shown in FIG. 1, the endoscope 1 is designed so that, when the flexible probe 13 is inserted into the channel 3e from the mouthpiece 2c and a front end of the casing 16 is abutted on the mouthpiece 2c, the distal end of the treatment unit 13a falls within the field of vision of the endoscope 1. Therefore, the endoscope 1 enables the ultrasonic treatment apparatus 10 to stably exhibit its performance and is excellent in usability.

Figure 4:
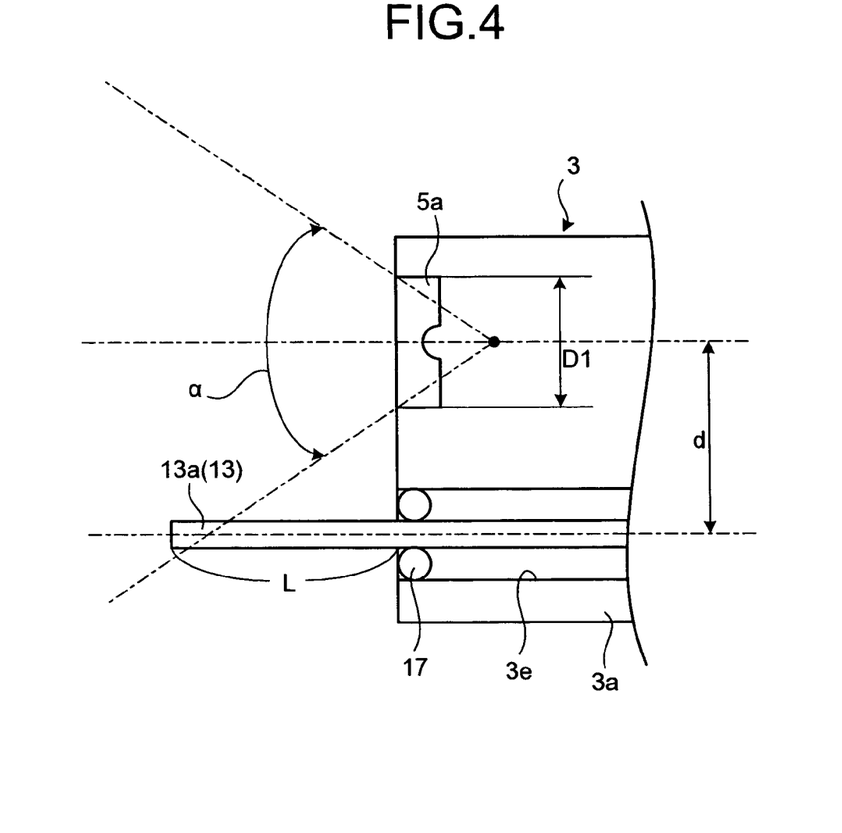
FIG. 4 is a typical view of a distal end of an inserted unit of the endoscope according to the first embodiment.

FIG. 4 is a typical view of a distal end of an inserted unit of the endoscope according to the first embodiment. As shown in FIG. 4, the endoscope 1 needs to satisfy the following Equation so that the distal end of the treatment unit 13a falls within the field of vision of the endoscope 1. In the Equation, $\alpha$ denotes an angle of view of the objective lens system 5a, D1 denotes a lens diameter on the distal end of the inserted unit 3, d denotes a distance between an optical axis of the objective lens system 5a and an axis of the flexible probe 13, and L denotes a protruding length of the treatment unit 13a from the distal end of the inserted unit 3.

$$L > (d - D1/2)/\tan(\alpha/2)$$

Figure 5:
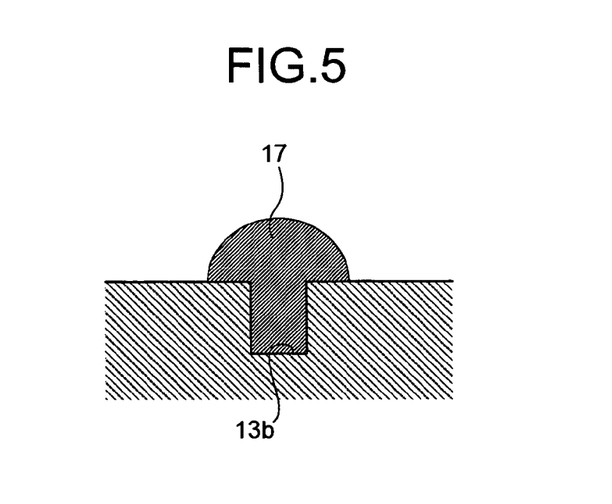
FIG. 5 is a cross-sectional view of a vibration isolating member attached to a flexible probe in one example.
Figure 6A:
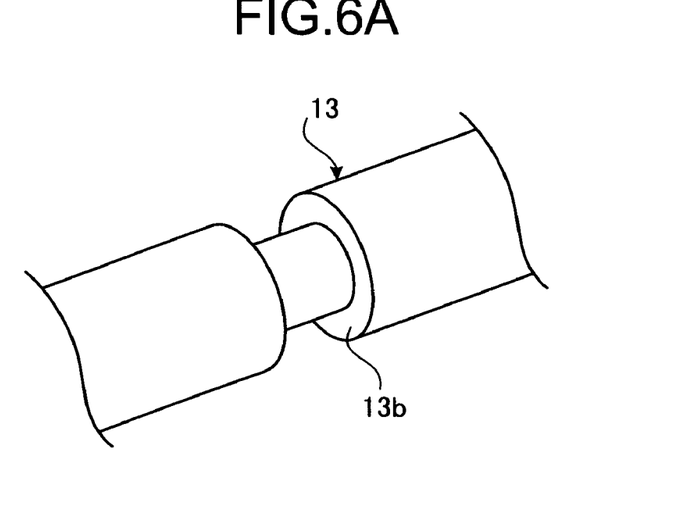
FIG. 6A is a perspective view of a concave portion into which a vibration isolating member is attached in another example.
Figure 6B:
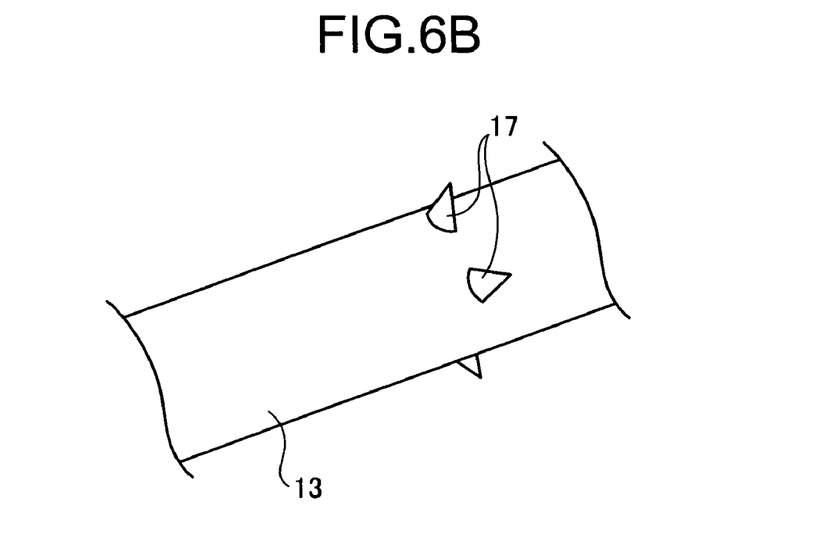
FIG. 6B is a perspective view of a vibration isolating member attached to a flexible probe in yet another example.

As shown in FIG. 2, the flexible probe 13 includes vibration isolating members 17 abutted on an inside surface of the channel 3e at positions corresponding to respective nodes of the ultrasonic vibration so as to suppress a noise vibration resulting from the transmitted ultrasonic vibration. Each vibration isolating member 17 may consist of a heat resistant material such as fluorocarbon resin, polyimide, or rubber. The vibration isolating member 17 may be attached into a concave portion 13b formed in the flexible probe 13 in a circumferential direction as shown in FIG. 5. By attaching such vibration isolating members 17, the endoscope 1 can suppress occurrence of the noise vibration to the flexible probe 13 and stably transmit the ultrasonic vibration using the flexible probe 13. Further, in the endoscope 1, although the vibration isolating members 17 contact with the channel 3e, the members 17 do not hamper an operation of the flexible probe 13 within the channel 3e and the flexible probe 13 can be, therefore, moved forward or backward within the channel 3e. In the flexible probe 13, the nodes of the ultrasonic vibration are points. However, as shown in FIG. 6A, the vibration isolating members 17 may be located within a range of several millimeters including the positions of the nodes by forming the concave portion 13b into a longitudinal groove extending in a longitudinal direction, and attaching the vibration isolating member 17 onto the concave portion 13b. Further, as shown in FIG. 6B, the vibration isolating members 17 may be provided on the outer periphery of the flexible probe 13 at circumferential intervals.

When the inserted unit 3 of the endoscope 1 is inserted from a mouth of a subject into the celomic cavity of, for example, the stomach or the small intestine and a treatment target site is confirmed by the eyepiece 2a, the flexible probe 13 is inserted from the mouthpiece 2c and the casing 16 is abutted on the mouthpiece 2c. Thus, the endoscope 1 is in a state in which the treatment unit 13a protrudes from the distal end of the inserted unit 3 into the field of vision of the endoscope 1. In this state, the position of the treatment unit 13a is adjusted while confirming the treatment target site with the eye piece 2a and a predetermined medical treatment is performed by the treatment unit 13a. In this way, the flexible probe 13 can be appropriately positioned within the field of vision of the endoscope 1. Therefore, the ultrasonic treatment apparatus 10 of the endoscope 1 can exhibit a required performance stably, and the endoscope 1 is far more excellent in usability than the conventional endoscope.

Figure 7:
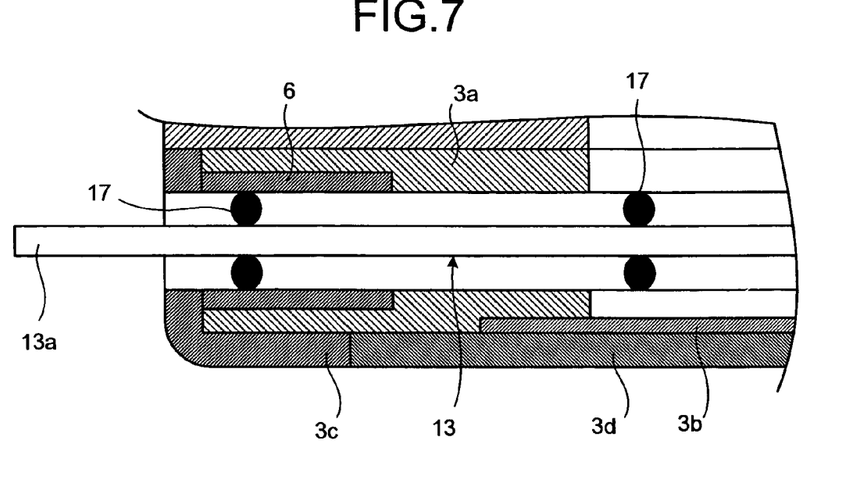
FIG. 7 is a cross-sectional view of a protection member attached to distal end hardware in one example.

Preferably, a protection coating consisting of fluorocarbon resin or the like is applied on the inside surface of the channel 3e by a length of $\lambda/4$ to $\lambda$ from the distal end side, where $\lambda$ denotes a wavelength of the ultrasonic vibration. If such a coating is applied, it is possible to prevent the distal end of the flexible probe 13 from being broken or damaged by the interference of the flexible probe 13 with the inside surface of the channel 3e and prevent the inside surface of the channel 3e from being damaged. This can thereby facilitate inserting the flexible probe 13 into the celomic cavity and improve usability of the endoscope 1. Alternatively, as shown in FIG. 7, a diameter of the channel 3e of distal end-side of the distal end hardware 3a may be enlarged in a radial direction, and a protection member 6 composed of a cylindrical body consisting of fluorocarbon resin, polyimide, or the like may be attached, in place of the protection coating, to the diameter-enlarged portion.

Figure 8:
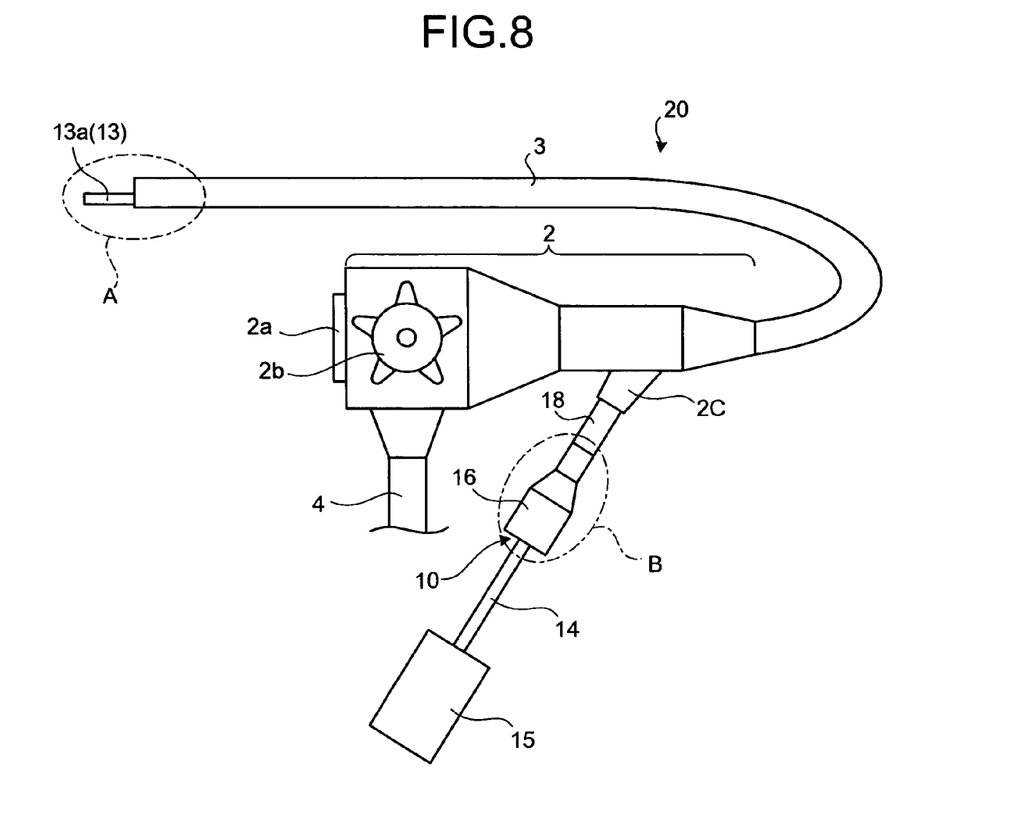
FIG. 8 is a schematic block diagram of an endoscope according to a second embodiment of the present invention.
Figure 9:
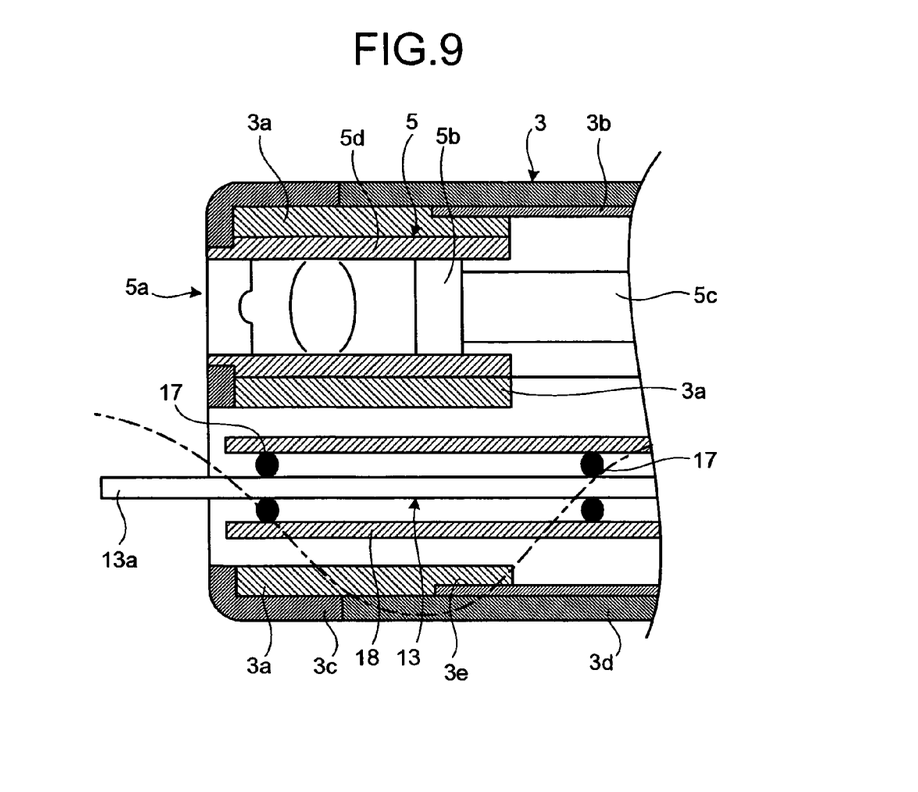
FIG. 9 is an enlarged cross-sectional view of a part A of the endoscope shown in FIG. 8.
Figure 10:
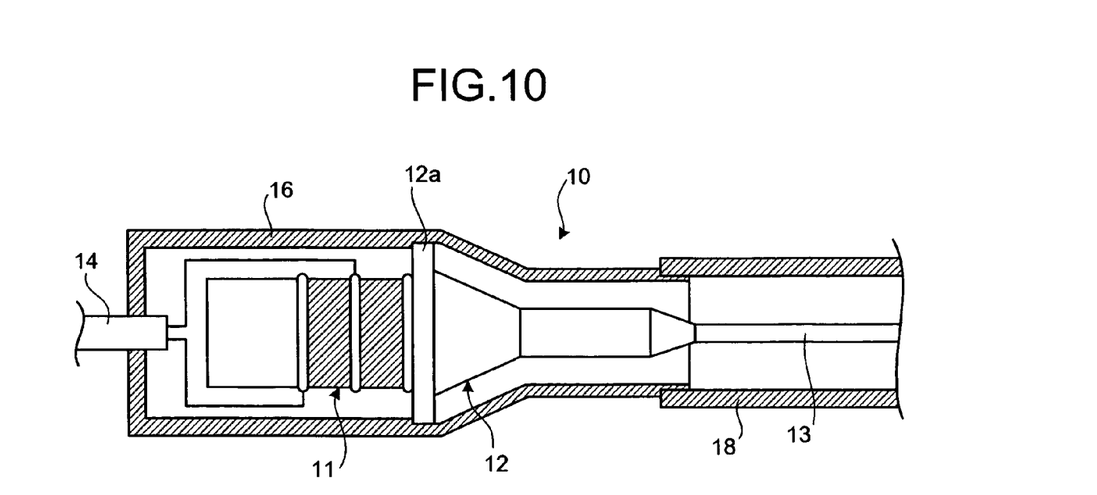
FIG. 10 is an enlarged cross-sectional view of a part B of the endoscope shown in FIG. 8.

An endoscope according to the second embodiment will be explained with reference to FIGS. 8 to 15. The endoscope 20 according to the second embodiment differs from the endoscope 1 according to the first embodiment in that the ultrasonic treatment apparatus 10 includes a sheath 18 which covers the flexible probe 13, and in that the flexible probe 13 together with the sheath 18 is inserted into the channel 3e. FIG. 8 is a schematic block diagram of an endoscope according to a second embodiment. FIG. 9 is an enlarged cross-sectional view of a part A of the endoscope 20 shown in FIG. 8. FIG. 10 is an enlarged cross-sectional view of a part B of the endoscope 20 shown in FIG. 8.

The sheath 18 is set so that the flexible probe 13 protrudes from the distal end of the inserted unit 3 by a length L. As shown in FIGS. 8 and 10, one end of the sheath 18 is connected to the casing 16 of the ultrasonic treatment apparatus 10, and the other end thereof is located near an open end within the channel 3e of the inserted unit 3.

In the endoscope 20, similarly to the endoscope 1, the protruding length L of the treatment unit 13a is set to satisfy the relationship of the Equation, that is, $L > (d-D1/2)/\tan(\alpha/2)$, whereby the distal end of the treatment unit 13a is arranged within the field of vision of the endoscope 20.

Figure 11:
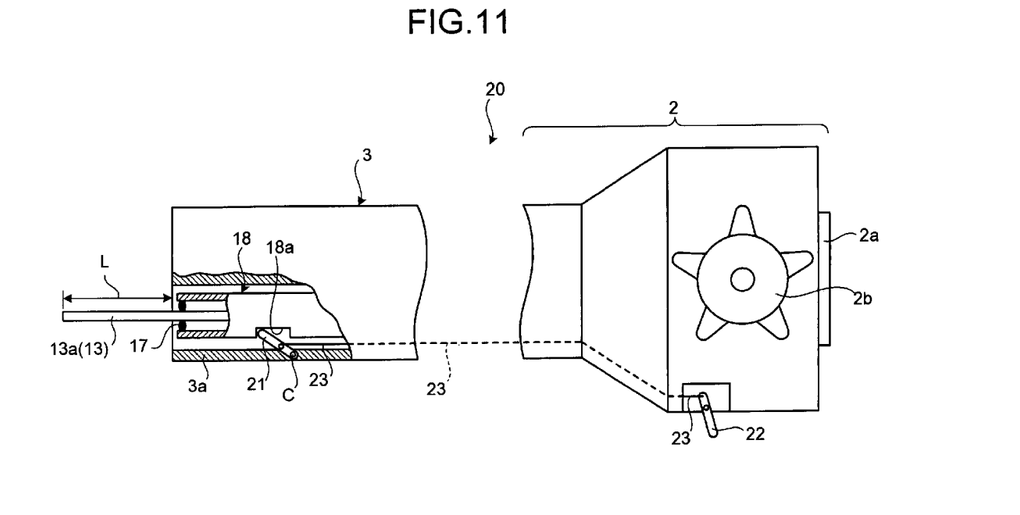
FIG. 11 is a front view of a positioning unit that positions a distal end of a treatment unit of a flexible probe of the endoscope according to the second embodiment while breaking important parts of the positioning unit.

As shown in FIG. 11, the endoscope 20 includes a stopper 21 which is provided near the distal end of the inserted unit 3, and which serves as a positioning unit that positions the treatment unit 13a to locate the distal end thereof within the field of vision of the endoscope 20. The stopper 21 includes an operation lever 22 provided on the operating unit 2 and a wire 23 having one end connected to the stopper 21 and the other end connected to the operation lever 22.

As shown in FIG. 11, the wire 23 is connected between a distal end and a rotation center C of the stopper 21. A lower end of the operation lever 22 is pressed toward the distal end of the inserted unit 3, whereby the stopper 21 is rotated clockwise through the wire 23 and built up. As a result, in the endoscope 20, the distal end of the stopper 21 is engaged with a concave portion 18a formed in the sheath 18, the flexible probe 13 or, therefore, the distal end of the treatment unit 13a is positioned within the field of vision of the endoscope 20. To disengage the distal end of the stopper 21 from the concave portion 18a, a lower end of the operation lever 22 is pulled, whereby the stopper 21 is rotated counterclockwise and gotten down and the distal end of the stopper 21 is disengaged from the concave portion 18a. The ultrasonic treatment apparatus 10 can move the flexible probe 13 together with the sheath 18 forward or backward within the channel 3e. As can be seen, in the endoscope 20, similarly to the endoscope 1, the distal end of the flexible probe 13 is positioned appropriately within the field of vision of the endoscope 20. Therefore, the endoscope 20 enables the ultrasonic treatment apparatus 10 to stably perform the required performance, and is far more excellent in usability than the conventional endoscope.

As shown in FIG. 9, the vibration isolating members 17 which are abut on an inside surface of the sheath 18 are provided at positions of nodes of the ultrasonic vibration, respectively, in the longitudinal direction in order to suppress the noise vibration resulting from the transmitted ultrasonic vibration. By providing the vibration isolating members 17, the endoscope 20 can suppress occurrence of the noise vibration to the flexible probe 13 even when the ultrasonic treatment apparatus 10 is used, and stably transmit the ultrasonic vibration by the flexible probe 13.

Figure 12:
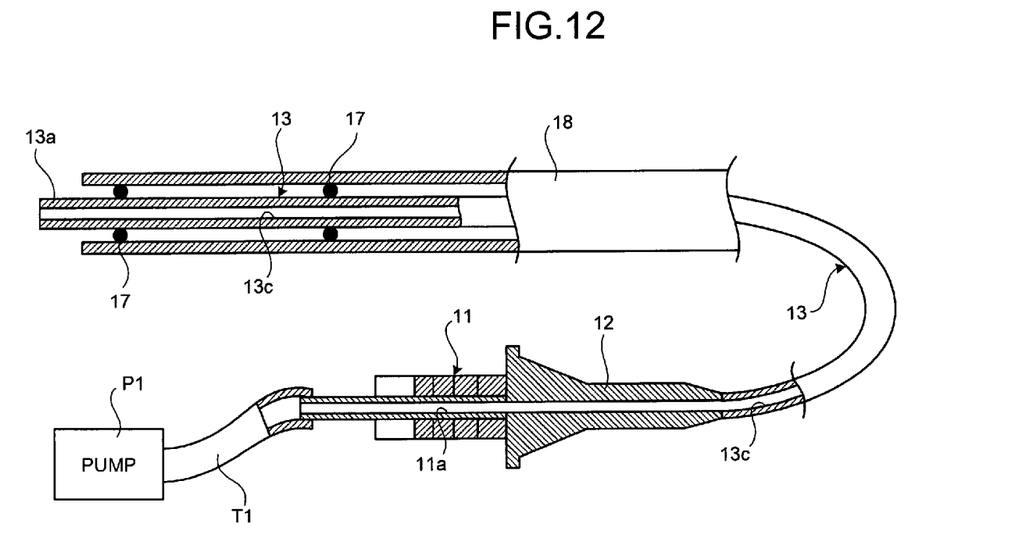
FIG. 12 is a schematic block diagram of a modification of an ultrasonic treatment apparatus employed in the endoscope according to the second embodiment while breaking a part of the ultrasonic treatment apparatus.

As shown in FIG. 12, the ultrasonic treatment apparatus 10 may be constituted so that suction holes 11a and 13c are formed in the ultrasonic vibrator 11 and the flexible probe 13 over their entire lengths, respectively, and a pump P1 may be connected to an end of the suction hole 11a of the ultrasonic vibrator 11 through a suction tube T1. By so constituting, the ultrasonic treatment apparatus 10 can suck in and remove broken particles of a living tissue emulsified and broken while performing a treatment on the affected part, thereby facilitating observing the affected part and further improving usability of the endoscope 20.

Figure 13:
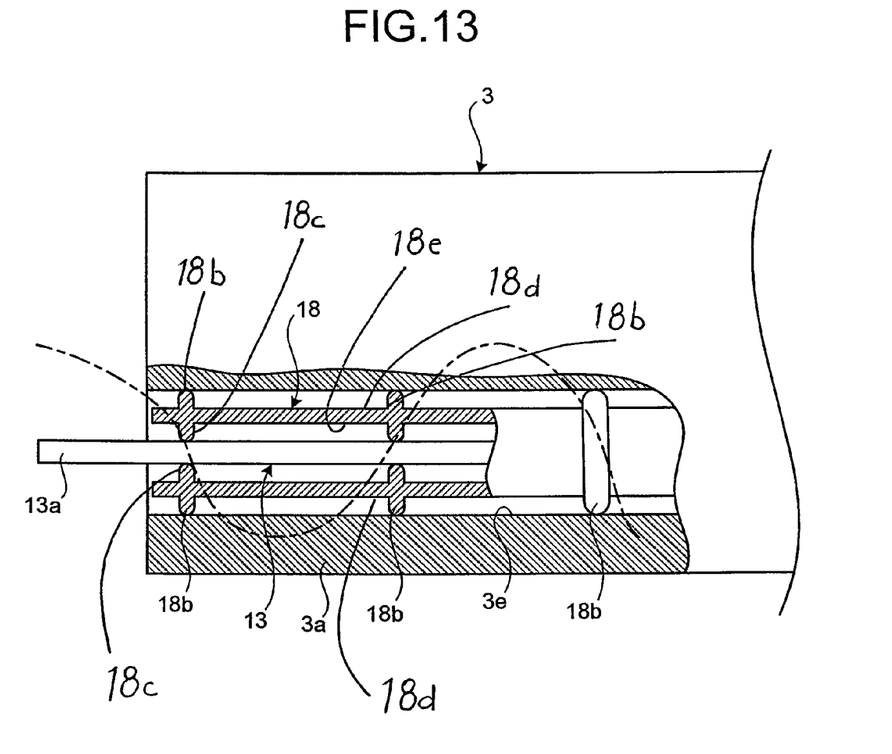
FIG. 13 is a schematic block diagram of a modification of the flexible probe employed in the ultrasonic treatment apparatus shown in FIG. 12 while partially breaking a distal end of the inserted unit of the endoscope.

As shown in FIG. 13, vibration isolating protrusions 18b abutted on the inside surface of the channel 3e and the flexible probe 13 may be entirely circumferentially provided on an inside surface and an outside surface of the sheath 18 which covers the flexible probe 13 at positions corresponding to the nodes of the ultrasonic vibration, respectively, in place of the vibration isolating members 17 provided on the flexible probe 13. The sheath 18 can suppress occurrence of the noise vibration to the flexible probe 13 by the vibration isolating protrusions 18b. Therefore, the flexible probe 13 can stably transmit the ultrasonic vibration. Preferably, the vibration isolating protrusions 18b are provided in at least two or more portions including the distal end of the sheath 18 with a view of suppressing the vibration of the flexible probe 13. In FIG. 13, as described above, the sheath 18 can be deemed to have an outer surface or skin 18d which has protrusions 18b and an inside surface or skin 18e which has the protrusions 18c. Thereby, it is inherent that the sheath with its protrusions provides isolation and vibration suppression or dampening both between the sheath and the flexible probe 13, as well as between the sheath and the channel 3.

Figure 14:
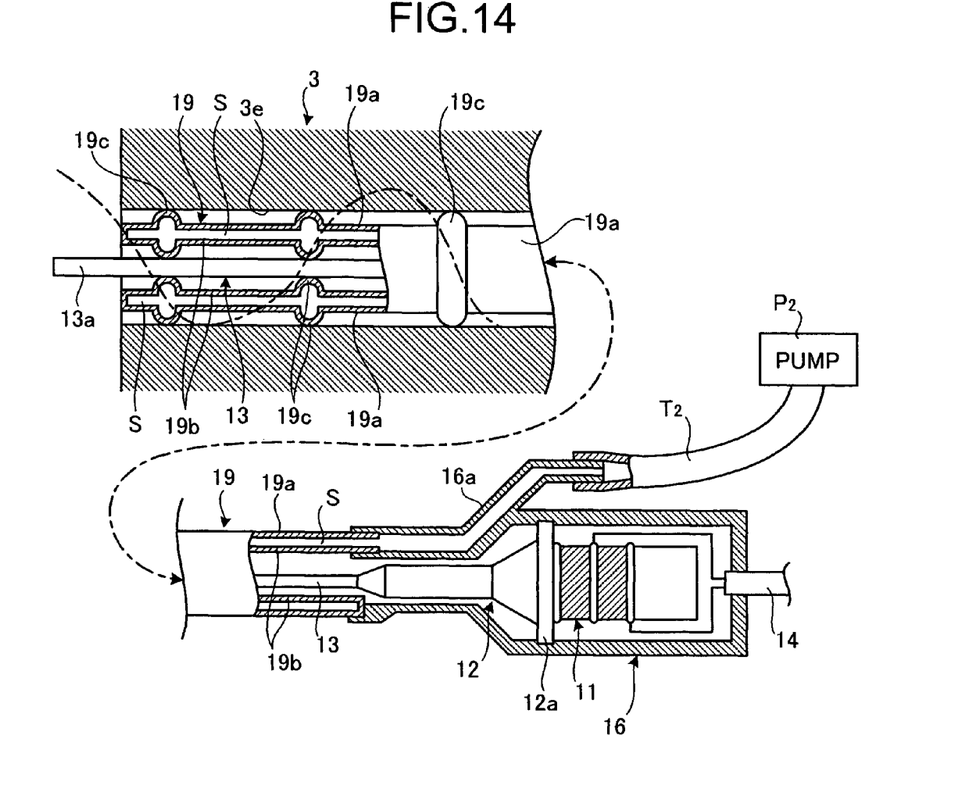
FIG. 14 is a schematic block diagram of a modification of a sheath which covers the flexible probe while partially breaking the endoscope.

Like a sheath 19 shown in FIG. 14, the sheath may be a cylindrical body having a double structure in which a space S is formed by an outer skin 19a and an inner skin 19b. According to this modification, the sheath 19 is inflated by the air supplied to the space S from an air pipe 16a provided in the casing 16 of the ultrasonic treatment apparatus 10, and formed into a cylindrical body. In addition, vibration isolating protrusions 19c abutted on the flexible probe 13 and the inside surface of the channel 3e are formed on an inside surface and an outside surface of the sheath 19 at positions corresponding to the nodes of the ultrasonic vibration, respectively. The air pipe 16a is connected to a pump P2 which supplies and evacuates the air to and from the space S through a tube T2.

Figure 15:
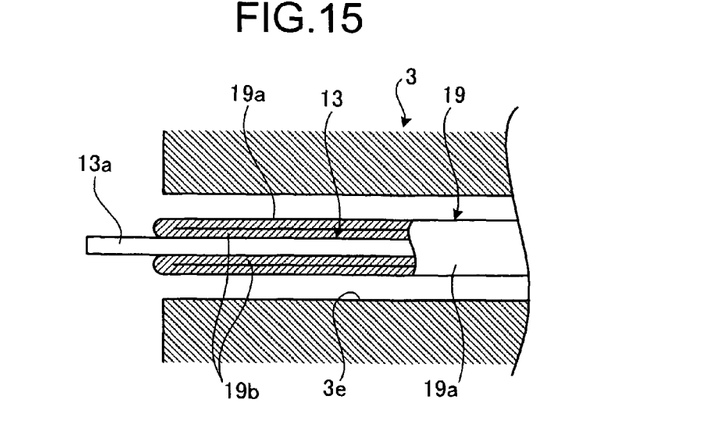
FIG. 15 is a partially broken view of the distal end of the inserted unit of the endoscope when the sheath shown in FIG. 14 is deflated.

When the air is evacuated by the air pump P2 from the space S, the sheath 19 is deflated as shown in FIG. 15. Therefore, the sheath 19 can be easily inserted into the channel 3e of the endoscope 20. Further, when the air is supplied to the space S by the air pump P2 during the treatment on the affected part by the ultrasonic treatment apparatus 10, the sheath 19 is inflated as shown in FIG. 14 and can suppress occurrence of the noise vibration to the flexible probe 13 by the vibration isolating protrusions 19c similarly to the sheath 18.

Figure 16:
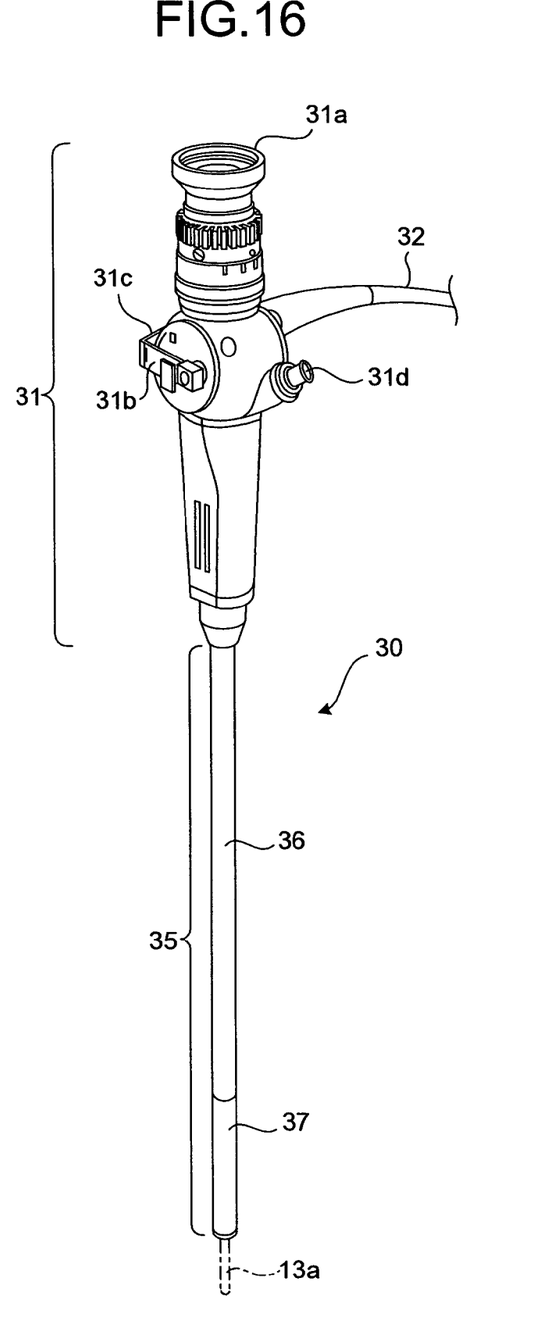
FIG. 16 is a schematic block diagram of an endoscope according to a third embodiment of the present invention.
Figure 17:
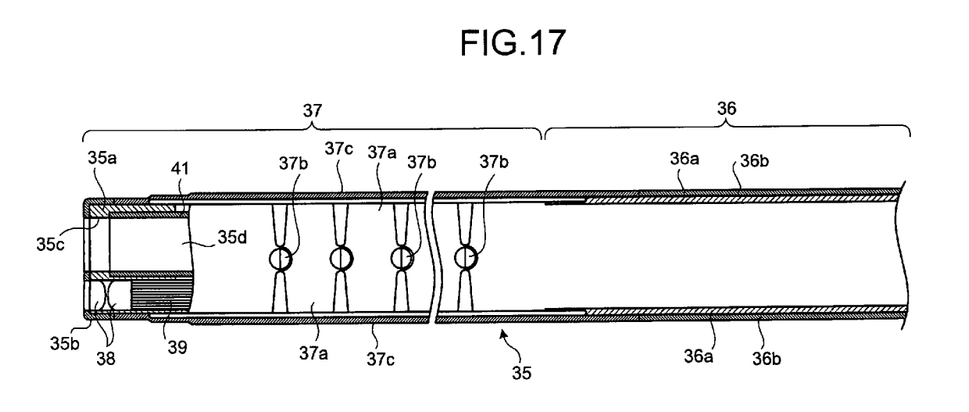
FIG. 17 is an enlarged cross-sectional view of an inserted unit of the endoscope shown in FIG. 16.

An endoscope according to a third embodiment will be explained. The endoscopes according to the first and the second embodiments are soft endoscopes each constituted so that the inserted unit 3 inserted into the celomic cavity of the body is bendable. The endoscope according to the third embodiment, by contrast, is a so-called rigid endoscope constituted so that the inserted unit inserted into the celomic cavity of the body includes a metallic sheath. FIG. 16 is a perspective view of schematic configuration of an endoscope 30 according to the third embodiment. FIG. 17 is a longitudinal sectional view of schematic configuration of the inserted unit of the endoscope 30 shown in FIG. 16. The endoscope 30 employs the same ultrasonic treatment apparatus 10 as those of the endoscopes 1 and 20 according to the first and the second embodiments.

As shown in FIG. 16, the endoscope 30 is a rigid endoscope which includes an operating unit 31, an inserted unit 35 connected to the operating unit 31, and the ultrasonic treatment apparatus 10. The inserted unit 35 inserted into the celomic cavity of the body is rigid.

As shown in FIG. 16, an exterior of the operating unit 31 is subjected to an electric isolating processing, and an angle mechanism (not shown) which operates a bent portion 37 of the inserted unit 35 to be bent by an operation wire (not shown) is included in the operating unit 31. The operating unit 31 has an eyepiece 31a provided on its end, and a light guide cable 32 is connected to substantially a center of the operating unit 31. The light guide cable 32 is connected to a light source apparatus (not shown). The operating unit 31 also includes a shaft of an operation lever 31b for operating the angle mechanism, and an operation hook 31c is provided near the operation lever 31b. The operating unit 31 further includes an insertion port 31d which is provided at a position near the operation lever 31b, and through which the flexible probe 13 of the ultrasonic treatment apparatus 10 as well as the sheath 18 is inserted into a channel 35d of the inserted unit 35.

As shown in FIG. 16, the inserted unit 35 includes a long and rigid sheath unit 36 and the bent portion 37 provided to be continuous with a distal end of the rigid sheath unit 36. As shown in FIG. 17, the rigid sheath unit 36 includes a metallic sheath 36a and an insulating tube 36b covering the metallic sheath 36a over its entire length. A plurality of bent bridges 37a are rotatably connected to the bent portion 37 through connecting units 37b, respectively. The bent bridges 37a are covered with an insulating material 37c such as rubber and formed to be freely bendable. A main body member 35a on a distal end of the inserted unit 35 is covered with an insulating cover 35b. An objective lens 38 and an illuminating lens (not shown) are provided on a front surface of the inserted unit 35.

One end of the objective lens 38 is abutted on the other end of an image guide fiber flux 39 connected to the eyepiece 31a. A tube 41 is inserted into the inserted unit 35. The tube 41 forms a channel 35d through which the ultrasonic treatment apparatus 10 is inserted into the celomic cavity, between the insertion port 31d of the operating unit 31 and an opening 35c formed in the main body member 35a.

In the ultrasonic treatment apparatus 10, the flexible probe 13 is inserted, together with the sheath 18, from the insertion port 31d, the distal end of the treatment unit 13a of the flexible probe 13 is positioned within the field of vision of the endoscope 30, and so that the flexible probe 13 is arranged, together with the sheath 18, within the channel 35d. In the endoscope 30, the insertion port 31d and the casing 16 constitute a positioning unit that positions the ultrasonic treatment apparatus 10. Namely, the endoscope 30 is designed in advance so as to satisfy these requirements by abutting a front end of the casing 16 on the insertion port 31d when the flexible probe 13 is inserted into the channel 35d from the insertion port 31d.

Figure 18:
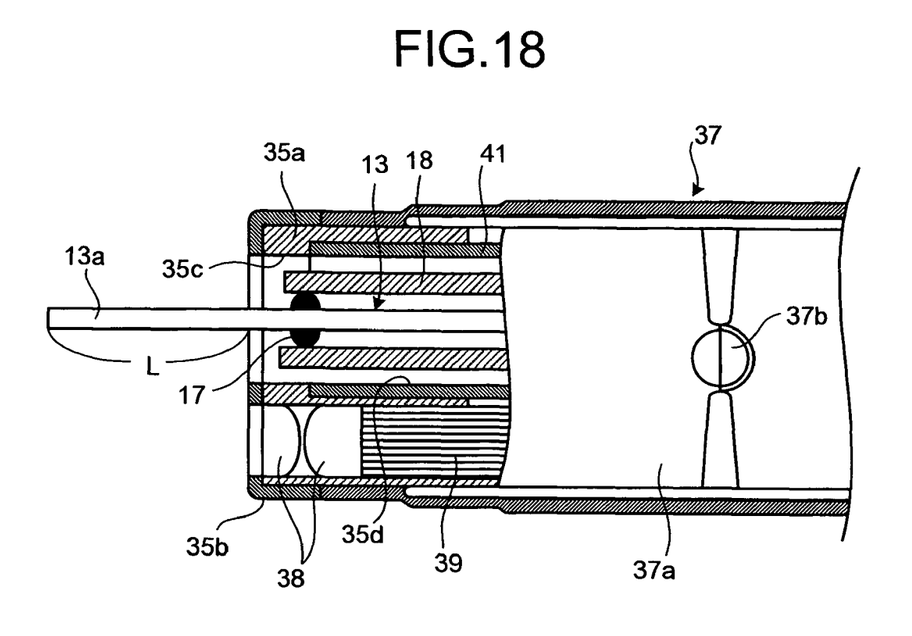
FIG. 18 is an enlarged view of the distal end of the inserted unit when the flexible probe is inserted into a channel of the inserted unit shown in FIG. 16.

As a result, when the ultrasonic treatment apparatus 10 is positioned by the insertion port 31d and the casing 16, which serve as the positioning unit, the distal end of the treatment unit 13a protrudes from the distal end of the endoscope 30 by the length L and the flexible probe 13 is positioned within the field of vision of the endoscope 30, as shown in FIG. 18. The protruding length L is set to satisfy the Equation, that is, $L > (d-D1/2)/\tan(\alpha/2)$ similarly to the first and the second embodiments. Therefore, the endoscope 30 enables the ultrasonic treatment apparatus 10 to stably exhibit its performance, and is excellent in usability.

The vibration isolating members 17 abutted on the inside surface of the sheath 18 are provided in the longitudinal direction at positions corresponding to the nodes of the transmitted ultrasonic vibration, respectively. Therefore, the endoscope 30 can suppress occurrence of the noise vibration to the flexible probe 13 even when the ultrasonic treatment apparatus 10 is used, and stably transmit the ultrasonic vibration by the flexible probe 13.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an inserted unit that is adapted to be inserted into a celomic cavity of a body and having therein at least one channel;
    a positioning unit that is provided near a distal end of the inserted unit; and
    an ultrasonic treatment apparatus that includes a transmitting member, a treatment unit, and a sheath, the transmitting member transmitting an ultrasonic wave produced by an ultrasonic vibrator, the treatment unit being provided on a distal end of the transmitting member, the sheath housing therein the transmitting member, wherein
    the ultrasonic treatment apparatus is movable forward or backward within the channel and is inserted into the channel to be arranged within the channel by engaging the positioning unit with the sheath so as to position a distal end of the treatment unit within a field of vision of the endoscope, and wherein the sheath has vibration isolating protrusions including at least one first protrusion extending from an inside surface of the sheath and abutting the transmitting member and at least one second protrusion extending from an outside surface of the sheath and abutting an inside surface of the channel, and said protrusions being provided at a position corresponding to a node of the ultrasonic wave.

2. The endoscope according to claim 1, wherein the sheath has a cylindrical body.

* * * * *